May 7, 1957 E. S. BOERNER Plant Pat. 1,599
ROSE PLANT
Filed Sept. 7, 1956
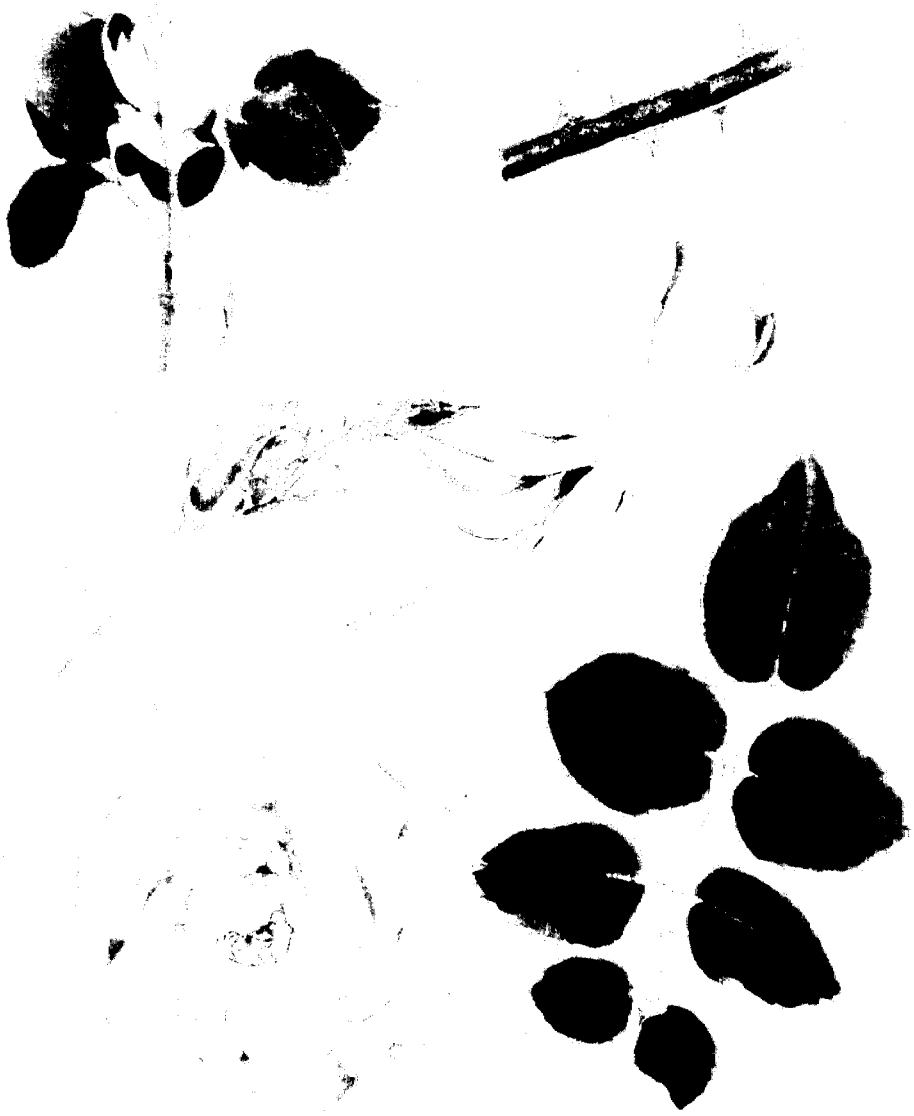
Inventor.
E. S. Boerner
By: Robb & Robb
Attorneys.

United States Patent Office

Plant Pat. 1,599

Patented May 7, 1957

1,599

ROSE PLANT

Eugene S. Boerner, Newark, N. Y., assignor to Jackson & Perkins Company, Newark, N. Y., a corporation of New York Application September 7, 1956, Serial No. 608,643

1 Claim. (Cl. 47—61)

The present invention relates to a new and distinct variety of rose plant of the hybrid tea class, which was originated by me by crossing an unnamed and unpatented seedling with the well-known variety "Peace" (Plant Patent No. 591).

The primary objective of this breeding was to produce a new rose variety characterized by its production of large flowers of Spinel Pink general color tonality, said flowers being borne on strong stems and being suitable for outdoor growing. This objective was fully achieved, along with other desirable improved characteristics which, considered altogether, constitute a new combination of characteristics in a rose of this class.

The primary features of the new variety include the following and definitely differentiate the new variety from its parents, as well as from all other varieties of which I am aware:

(1) The development of leaves of very large size as the growing season progresses;

(2) The large size of its flowers;

(3) Its strong flower stems;

(4) A unique quilling of the flower petals which gradually spreads throughout the entire flower and extends to the outside petals as the flower reaches its final opening stages;

(5) The distinctive wild rose fragrance of its flowers; and (6) The distinctive Spinel Pink general color tonality of the flowers which is unique in a rose of its size.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of 1945.
*Pollen parent.*—"Peace."

Classification:

*Botanic.*—Hybrid tea.
*Commercial.*—Hybrid tea.

*Flower*

(Observations made from specimens grown outdoors at Newark, New York, about mid-morning in the early part of September.)

Blooming habit: Recurrent—continuous.

Bud:

*Size.*—Very large.
*Form.*—Globular; is not affected by wet or hot weather.
*Color.*—When sepals first divide—Amaranth Purple, Plate 12. When petals begin to unfurl—Spinel Red, Plate 26, lightly overcast with Amaranth Purple, Plate 12. When half-blown: inside of petals—Tyrian Rose, Plate 12; reverse of petals—Rose Red, Plate 12, lightly overcast with Rose Color, Plate 12.
*Sepals.*—Slightly branched; curl back when petals begin to unfurl. Color: inside—Pale Turtle Green, Plate 32; outside—Light Bice Green, Plate 17.
*Calyx.*—Color—Biscay Green, Plate 17. Shape—apple. Size—broad. Aspect—smooth. Odor when rubbed—none.
*Peduncle.*—Length—long. Aspect—rough. Strength—stiff; heavy. Color—Biscay Green, Plate 17.
*Opening.*—Opens up well; is not affected by adverse weather conditions.

Bloom:

*Size.*—Very large. Average size when fully expanded—from 5½ to 6½ inches.
*Borne.*—Several together.
*Stems.*—Medium length; strong.
*Form (when first open).*—Cupped. Permanence—retains its form to the end, but outer petals curl back and quill.
*Petalage.*—Double (full but open center). Number of petals under normal conditions—from 60 to 65.
*Color.*—Center of flower—Spinel Pink, Plate 26. Outer petals—Thulite Pink, Plate 26, lightly overcast with Deep Rose Pink, Plate 12. Base of petals (aiglet)—Pale Lemon Yellow, Plate 4. Inside of petals—Spinel Pink, Plate 26, lightly overcast with Thulite Pink, Plate 26. Reverse of petals—Deep Rose Pink, Plate 12, lightly overcast with Rose Pink, Plate 12. General tonality from a distance—Spinel Pink, Plate 26, lightly overcast with Thulite Pink, Plate 26.
*Discoloration.*—General tonality at end of first day—Spinel Pink, Plate 26. Second day—Spinel Pink, Plate 26, lightly overcast with Thulite Pink, Plate 26. Third day—Thulite Pink, Plate 26, lightly overcast with Rose Pink, Plate 12.

Petals:

*Texture.*—Thick; is not affected by wet or hot weather.
*Appearance.*—Inside—velvety. Outside—shiny.
*Form.*—Round; slightly notched.
*Arrangement.*—Flat (with "rags" in center).
*Petaloids in center.*—Few; large.
*Persistence.*—Drop off cleanly.
*Fragrance.*—Moderate. Nature—wild rose.
*Lasting quality.*—On the plant—long. As cut flower—long.

*Genital organs*

Stamens, anthers: Large; many; regularly arranged around styles. Color—Cadmium Yellow, Plate 3.
Stamens, filaments (threads): Medium length. Color—Nopal Red, Plate 1.
Pollen: Color—Pale Orange Yellow, Plate 3.
Styles: Loosely separated; uneven length; medium length; thin.

Stigmas: Color—Maize Yellow, Plate 4.
Ovaries: All enclosed in calyx.
Hips: None.
Seeds: None.

*Plant*

Form: Bush.

Growth: Vigorous; upright.

Foliage: Compound of 5 to 7 leaflets.

*Size.*—From large to very large.
*Quantity.*—Normal.
*Color.*—New foliage: upper side—Cedar Green, Plate 6, with serrations of Vinaceous Purple, Plate 38; under side—Yellowish Oil Green, Plate 5, lightly overcast with Deep Hellebore Red, Plate 38. Old foliage: upper side—Dark Dull Yellow Green, Plate 32; under side—Light Elm Green, Plate 17.
*Shape.*—Oval pointed.
*Texture.*—Upper side—leathery. Underside—smooth.
*Ribs and veins.*—Ordinary.
*Edge.*—Serrated (saw-toothed).
*Serration.*—Both double and single; small.
*Leaf stem.*—Color—Corydalis Green, Plate 41. Under side—prickly.
*Stipules.*—Long; bearded.

Wood:

*New wood.*—Color—Hellebore Red, Plate 38. Bark—smooth.
*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; hooked downward. Color (when young)—Amaranth Purple, Plate 12. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by its development of leaves of very large size as the growing season progresses, its large flowers, its strong flower stems, the distinctive quilling of its flower petals which gradually spreads throughout the entire flower and extends to the outside petals as the flowers reach the final stages of opening, the distinctive wild rose fragrance of its flowers, and the distinctive Spinel Pink general color tonality of its flowers.

No references cited.